United States Patent
Moradian et al.

(10) Patent No.: US 11,752,035 B2
(45) Date of Patent: Sep. 12, 2023

(54) ULTRASONIC NEEDLES AND TRANSDUCER ASSEMBLIES FORMED OF NON-METAL MATERIALS OR A COMBINATION OF MATERIALS

(71) Applicant: Bausch & Lomb Incorporated, Rochester, NY (US)

(72) Inventors: Ala Moradian, St. Louis, MO (US); Brian D. McCary, Clayton, MO (US); Toh Seng Goh, Wildwood, MO (US); Matthew J. Fitzgerald, St. Louis, MO (US)

(73) Assignee: BAUSCH & LOMB INCORPORATED, Rochester, NY (US)

( * ) Notice: Subject to any disclaimer, the term of this patent is extended or adjusted under 35 U.S.C. 154(b) by 401 days.

(21) Appl. No.: 17/158,562

(22) Filed: Jan. 26, 2021

(65) Prior Publication Data

US 2021/0145639 A1 May 20, 2021

Related U.S. Application Data

(63) Continuation of application No. 14/690,791, filed on Apr. 20, 2015, now Pat. No. 10,932,948.

(51) Int. Cl.
*A61F 9/007* (2006.01)
(52) U.S. Cl.
CPC ................ *A61F 9/00745* (2013.01)
(58) Field of Classification Search
CPC . A61B 2017/320072; A61B 17/320068; A61F 9/00745; A61F 9/007
See application file for complete search history.

(56) References Cited

U.S. PATENT DOCUMENTS 4,764,165 A 8/1988 Reimels et al.
5,162,044 A * 11/1992 Gahn .................. A61F 9/00745
606/128

(Continued)

FOREIGN PATENT DOCUMENTS

CN 104055620 A 9/2014
EP 2011458 A1 1/2009

(Continued)

OTHER PUBLICATIONS

International Search Report and Written Opinion for PCT/US2016/27204 dated Jul. 15, 2016 pp. 10.

(Continued)

*Primary Examiner* — Diane D Yabut
*Assistant Examiner* — Christina C Lauer
(74) *Attorney, Agent, or Firm* — Harness, Dickey & Pierce, P.L.C.

(57) ABSTRACT

A phacoemulsification transducer assembly includes a reflector and a driver connected to the reflector. The driver has a known driver vibration frequency range. A horn is connected to the driver opposite the reflector. A needle is connected to the horn opposite the driver. The needle has a known free shaft length. To maximize a desired stroke length of the needle for a minimal amount of power applied to the driver, a material forming the needle is chosen such that a speed of sound through the material results in a quarter-wavelength distance at the driver vibration frequency range substantially equal to the needle free shaft length.

3 Claims, 2 Drawing Sheets

(56) References Cited

U.S. PATENT DOCUMENTS

Figure 1:
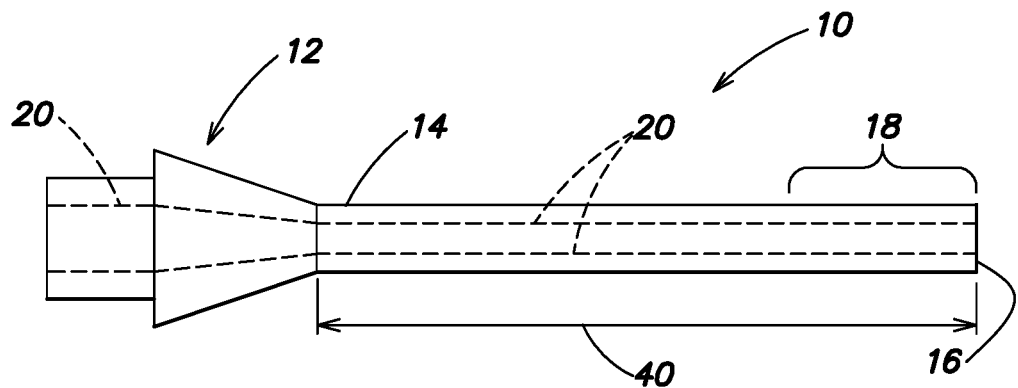

| | | | |
|---|---|---|---|
| 5,505,693 A | | 4/1996 | Mackool |
| 5,718,677 A | | 2/1998 | Capetan et al. |
| 5,853,290 A | | 12/1998 | Winston |
| 5,989,209 A | * | 11/1999 | Barrett ............... A61F 9/00745 606/107 |
| 7,189,245 B2 | | 3/2007 | Kaplan |
| 7,588,533 B2 | | 9/2009 | Drysdale |
| 7,588,553 B2 | * | 9/2009 | Dewey ............... A61F 9/00745 606/107 |
| 2003/0139809 A1 | | 7/2003 | Worst et al. |
| 2004/0126738 A1 | | 7/2004 | Atkin et al. |
| 2006/0094627 A1 | | 5/2006 | Mouser et al. |
| 2009/0236938 A1 | * | 9/2009 | Bromfield ............ B06B 1/0611 310/323.19 |
| 2009/0312775 A1 | | 12/2009 | Gilkey et al. |
| 2010/0036388 A1 | | 2/2010 | Gomez |
| 2010/0160852 A1 | * | 6/2010 | Moore, Jr. .......... A61F 9/00745 604/22 |
| 2011/0201995 A1 | | 8/2011 | Nallakrishnan |
| 2011/0314919 A1 | | 12/2011 | Ehlert et al. |
| 2013/0204285 A1 | | 8/2013 | Gouery et al. |
| 2013/0253557 A1 | * | 9/2013 | Urich ................. A61F 9/00745 606/169 |
| 2014/0364799 A1 | | 12/2014 | Beauvais et al. |
| 2014/0367499 A1 | | 12/2014 | Odenthal et al. |
| 2015/0112356 A1 | | 4/2015 | Chon et al. |
| 2016/0302816 A1 | | 10/2016 | Clayton |

FOREIGN PATENT DOCUMENTS

| | | |
|---|---|---|
| JP | S63-260552 A | 10/1988 |
| JP | H10-225476 A | 8/1998 |
| JP | 2002165881 A | 6/2002 |
| JP | 2005517468 A | 6/2005 |
| WO | WO-8701926 A1 | 4/1987 |
| WO | WO-9607377 A1 | 3/1996 |

OTHER PUBLICATIONS

European Search Report and Written Opinion for European Patent Application No. 16 78 3613.9, dated Jan. 2, 2019 pp. 7.
Japanese Office Action for Japanese Patent Application No. 2017-550702 dated Feb. 12, 2020 pp. 3.
International Preliminary Report on Patentability for PCT/US2016/027204, dated Jun. 14, 2017 pp. 12.

* cited by examiner

ULTRASONIC NEEDLES AND TRANSDUCER ASSEMBLIES FORMED OF NON-METAL MATERIALS OR A COMBINATION OF MATERIALS

CROSS-REFERENCE TO RELATED APPLICATIONS

This application is a continuation of U.S. patent application Ser. No. 14/690,791 filed on Apr. 20, 2015. The entire disclosure of the above application is incorporated herein by reference.

FIELD

The present disclosure relates to ultrasonic needles used in surgery, particularly ophthalmic surgery. More specifically, the present disclosure relates to ultrasonic needles formed of non-metal materials or a combination of materials.

BACKGROUND

This section provides background information related to the present disclosure which is not necessarily prior art.

Ultrasonic needles and transducer assemblies are known to be used for emulsifying and aspirating cataracts and other tissue from eyes, especially phacoemulsification (phaco) needles. These needles and transducer assemblies have traditionally been formed of metal, e.g. stainless steel, or most typically titanium. The metal needles withstand the strains of the ultrasonic vibrations, are very hard for breaking-up tissue, and rarely fracture (ensuring no particulate is lost in the eye), among other positive attributes. However, metal may produce excessive heat during vibration, potentially causing thermal burns on the cornea. In addition, metal is relatively difficult to form into the very small needles needed for eye surgery and is expensive to fabricate into needles often requiring machining rather than more cost-effective methods. Metal needles also require relatively large drive powers that limit the handpiece design choices.

There is scant known disclosure of alternate phaco needle materials other than metal. In practice, non-metal phaco needles essentially do not exist. There have been vague, single sentence mentions of phaco needles formed from materials other than titanium, but with no specificity or guidance regarding material selection criteria. For example, U.S. Pat. No. 7,588,533 to Dewey mentions that certain ribs may be made from a variety of materials such as ceramic or carbon fiber composites, polymers, or standard titanium. U.S. Pat. No. 5,989,209 to Barrett states that a phaco needle may be made from titanium stainless steel, a suitably tough plastic composite, or a combination thereof. There is no known teaching regarding how any materials might differ from metal, especially titanium in designing a phaco needle.

Therefore, there is a need for ultrasonic needles and transducer assemblies formed or partially formed of non-metal materials.

SUMMARY

This section provides a general summary of the disclosure, and is not a comprehensive disclosure of its full scope or all of its features.

Example phaco needles may include a hub for connection to an ultrasonic handpiece; an elongated shaft, formed with the hub, extending from the hub; where a distal end of the shaft breaks-up tissue when the distal end is caused to be vibrated by the handpiece. At least a distal portion of the shaft is formed of a material that has properties providing advantages compared to a metal needle. Example properties of materials for phaco needles may include a substantially lower density, a substantially higher electrical resistivity, a substantially lower thermal conductivity, a substantially lower mechanical lateral stiffness, a substantially higher efficiency of converting electrical energy powering the handpiece into motion of the distal end, a substantially lower acoustical impedance, a substantially higher Poisson's ratio, and a substantially higher mechanical gain.

An example phaco transducer assembly may include a reflector; a driver connected to the reflector for vibrating at a range of frequencies and at a known power level; a horn connected to the driver opposite the reflector; and a needle connected to the horn opposite the driver and having a distal end and having a free shaft length substantially equal to a quarter-wavelength of the speed of sound through materials forming the needle at the driver vibrating range of frequencies. An example construction of the transducer assembly to achieve a desired stroke length at the distal end depends on at least three factors including the driver vibrating range of frequencies, the free shaft length of the needle, and the materials forming the needle; such that for any two of the three factors known, the remaining third factor may be determined.

Another example phaco transducer assembly may include a reflector; a driver connected to the reflector, the driver having a known driver vibration frequency range; a horn connected to the driver opposite the reflector; a needle connected to the horn opposite the driver, the needle having a known free shaft length. To maximize a desired stroke length of the needle for a minimal amount of power applied to the driver, a material forming the needle is chosen such that a speed of sound through the material results in a quarter-wavelength distance at the driver vibration frequency range substantially equal to the needle free shaft length.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
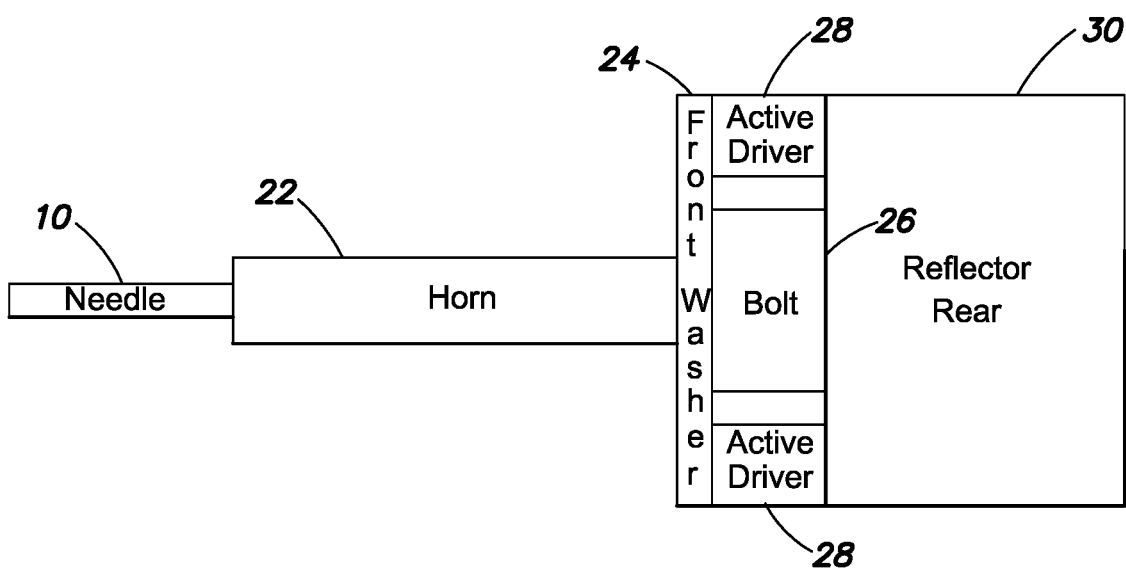
Figure 3:
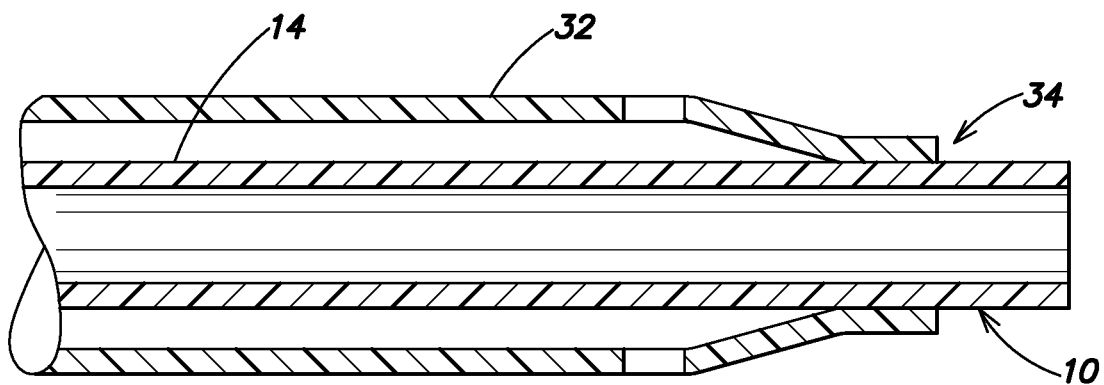
Figure 4:
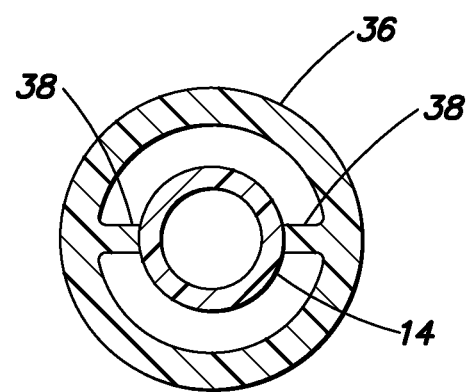

FIG. 1 is an elevation of an example needle;
FIG. 2 is a block view of an example transducer assembly;
FIG. 3 is a partial cross-section of a needle and sleeve example; and
FIG. 4 is a cross-section of another needle and sleeve example.

Corresponding reference numerals indicate corresponding parts throughout the several views of the drawings.

DETAILED DESCRIPTION

Example embodiments will now be described more fully with reference to the accompanying drawings.

A phacoemulsification (phaco) needle 10, shown in FIG. 1, may include a hub 12 for connection to an ultrasonic handpiece (unshown). The term phacoemulsification or phaco needle or phaco transducer or other reference to phaco, as used in this disclosure includes any ultrasonic ophthalmic surgery for vibrating a needle, including for cataract removal, other anterior surgeries, or for posterior surgery, such as fragmentation, vitrectomy, etc. The ultrasonic handpiece may be of any suitable construction and is well-known for causing ultrasonic vibratory motion of the phaco needle 10. An elongated shaft 14 is formed with the hub 12 and extending from the hub 12. A distal end 16 of the shaft 14 breaks-up tissue when the distal end 16 is caused to be vibrated by the handpiece. At least a distal portion, shown generally at 18, of the shaft 14 is formed of a material having a substantially lower density compared to a metal needle. The needle 10 may also have a lumen spanning a length of the needle 10, as indicated by the dashed lines 20. The needle 10 may be of any suitable form factor, such a straight needle shown, or other form factors as are known and desired by a user. For example, the shaft 14 could be curved, straight, have a flared distal end, have a varying lumen diameter, internal or external ridges, offset with respect a longitudinal axis of hub 12, or other shape as desired.

Ultrasonic phaco needle 10 may be for use in cataract emulsification or fragmentation and made from a material with a low density fitting onto known phaco handpieces. Phaco needle 10 may also be for use in vitrectomy and connected to an ultrasonic handpiece for removing vitreous from an eye. The needle 10's lower mass reduces the energy stored in the reciprocating system. The reciprocating or ultrasonic system may include the needle 10, a horn 22, a front washer 24, a bolt 26 surrounded by one or more drivers 28, and a reflector 30, as shown in FIG. 2. The ultrasonic system is shown in a cross-section block view and therefore certain details are not shown. For example, needle 10 is shown without a hub, as a hub may not be necessary for needles formed integrally with horn 22. Driver 28 may be one or more piezo-electric transducers or magneto-resistive transducers, or any other devices that may produce vibration of needle 10. The lower density of at least a portion of needle 10, compared to a density of a metal needle, may also reduce the power required to drive the handpiece at a desired stroke amplitude. Phaco handpieces and needle geometry are generally known to those skilled in the art of ultrasonic ophthalmic surgery. Example needles of a lower density were built from a plastic material, specifically polyether ether ketone (PEEK), a high performance plastic suitable for surgery. The PEEK needles have a density about 1320 kilograms per meter cubed ($kg/m^3$), substantially less than the 4500 $kg/m^3$ density of known titanium phaco needles. Benchtop testing of the PEEK needles exhibited relatively large strokes at low power levels compared to the stroke of known titanium needles. Needle 10 material density values less than 4000 $kg/m^3$ would reduce the needle reciprocating mass by at least 5%, and the energy in the needle reciprocating mass by at least 10%, and such needle materials may be regarded as having a substantially lower density compared to a metal needle.

As mentioned above, an alternate example may include a handpiece that does not have a separately formed and removable needle, rather the needle may be formed integrally with horn 22. Viewed another way, this may be described as a handpiece without a discernable needle and where a portion of horn 22 is for contact with the surgical site, e.g. an eye. In this alternate example, a selection of the material forming the horn that has a substantially lower density compared to known metal horns may provide similar benefits of the lower density needle.

During operation, such as cataract surgery, the needle attached to the handpiece reciprocates in some manner, e.g. back and forth, side-to-side, in an elliptical manner, or other motion. The needle stores energy, in the form of the kinetic energy of the mass of the needle, at maximum velocity (mid-stroke). At each end of the stroke, this kinetic energy must be turned into potential energy, in the transducer mechanism that is under tension or compression. This energy transformation, from kinetic to potential, ultimately consumes power. Furthermore, for piezoelectric transducer crystals, the force required to drive the needle mass is generally proportional to the pressure in the transducer crystals multiplied by the transducer crystal area and is, in turn, proportional to the voltage across the transducer crystals. Higher needle masses require higher drive forces, i.e. larger crystals, higher drive voltages, or both. Use of a lower density material reduces the needle reciprocating mass in the system, thus reducing the transducer and drive requirements. Reducing the transducer and drive requirements may lead to less energy needed to effectively achieve the surgical goals, which some believe may lead to better surgical outcomes. The reduced transducer and drive requirements may also allow for cost improvements in the phaco handpiece, and in the drive circuits. Further, if smaller transducer crystals are used an ergonomic improvement in handpiece design may be possible through lighter and smaller handpieces.

Examples in accordance with the above, may also allow for a needle or at least the distal portion to be substantially transparent. The needle may be entirely formed of the material having the substantially lower density compared to the metal needle. Further, a horn of the handpiece may also be formed of the material having the substantially lower density compared to the metal needle. The needle or at least the distal portion may be formed of a plastic material. The term plastic as used in this example disclosure has its ordinary dictionary meaning, i.e. any of a group of synthetic or natural organic materials that may be shaped when soft and then hardened, including many types of resins, resinoids, polymers, cellulose derivatives, casein materials, proteins, etc.

Another example of the material having the substantially lower density compared to the known metal needles is the material has a density of less than 4000 $kg/m^3$. A further example of the material having the substantially lower density compared to the metal needle is the material has a density of less than 3000 $kg/m^3$. Still another example of the material having the substantially lower density compared to the metal needle is the material has a density of less than 2000 $kg/m^3$.

Using a material having a substantially lower density compared to the known metal needles may allow an example where an irrigation sleeve 32 is integrally molded with at least the distal portion of the needle 10, specifically shaft 14, as shown in FIG. 3 at 34. The sleeve and needle may be formed together using any known molding techniques or the sleeve may be integrally molded with the needle using known adhesives or other materials for attaching plastic materials together. Another example of an irrigation sleeve 36 integrally molded with the needle shaft 14 is shown in FIG. 4, where ribs 38 are molded onto and between needle shaft 14 and sleeve 36. The ribs 38 provide support for sleeve 36 and may assist in maintaining a fluid flow path between the sleeve and needle. The number of ribs 38 may be more than shown, depending on the design requirements.

Another example phaco needle includes a hub for connection to an ultrasonic handpiece and an elongated shaft formed with the hub and extending from the hub wherein a distal end of the shaft breaks-up tissue when the distal end is caused to be vibrated by the handpiece. This example phaco needle further includes at least a distal portion of the shaft formed of a material having a substantially higher electrical resistivity compared to a metal needle. A phaco needle formed of a material having a substantially higher electrical resistivity relative to known metal phaco needles provides electrical isolation from the phaco drive circuits and transformers.

Example phaco needles formed of a substantially higher electrical resistivity may have the same properties described above with respect to needle 10. That is the example needles may be transparent, may have integrally formed irrigation sleeves, may be formed of PEEK or other plastic materials, etc. Further, the material having the substantially higher electrical resistivity compared to the metal needle may have an electrical resistivity greater than 1 µΩ·m (micro-ohm·meters). Still further, the material having the substantially higher electrical resistivity compared to the metal needle may have an electrical resistivity greater than 500,000 µΩ·m. A typical known titanium phaco needle has a bulk resistivity of about 0.5 µΩ·m and therefore, materials with resistivity values above about 1 µΩ·m may be regarded as having substantially higher electrical resistivity. Another way to view the issue is with respect to the resistivity of the saline solution and natural tissue and fluids of the eye. It may be estimated that the saline solution and fluids of the eye have a bulk resistivity of about 200,000 µΩ·m and therefore, materials with resistivities above about 500,000 µΩ·m may be regarded as having substantially higher electrical resistivity.

During surgery, e.g. ophthalmic cataract surgery, a handpiece is in electrical contact with the patient's eye. The handpiece is typically electrically isolated from its drive system and the voltage applied to the transducer in the handpiece appears as a high impedance, high voltage, high frequency signal at the needle tip. The patient is frequently attached to a physiological monitor, including an electrocardiogram (EKG), and monitors respiration, heart rate, oxygen saturation, and possibly other vital signs. Experience has shown that in certain pulsed modes at certain pulse rates, the software algorithms in the patient monitors may detect the start of a voltage on the needle via conduction through the body and falsely interpret or identify it as a potential danger to the patient. Use of a needle at least partially formed of a material having the substantially higher electrical resistivity compared to the metal needle decreases conductively coupled noise, limiting or eliminating these false danger warnings.

A further example phaco needle may include a hub for connection to an ultrasonic handpiece and an elongated shaft formed with the hub and extending from the hub wherein a distal end of the shaft breaks-up tissue when the distal end is caused to be vibrated by the handpiece, as described above. This further example includes at least a distal portion of the shaft may be formed of a material having a substantially lower thermal conductivity compared to a metal needle.

Example phaco needles formed of material having a substantially lower thermal conductivity may have the same properties described above with respect to needle 10. That is the example needles may be transparent, may have integrally formed irrigation sleeves, may be formed of PEEK or other plastic materials, etc. Further, the material having the substantially lower thermal conductivity compared to the metal needle may have a thermal conductivity less than 18 W/m·K (watts per meter·Kelvin). Still further, the material having the substantially lower thermal conductivity compared to the metal needle may have a thermal conductivity less than 10 W/m·K. Still another example is where the material having the substantially lower thermal conductivity compared to the metal needle may have a thermal conductivity less than 5 W/m·K. Yet another example is where the material having the substantially lower thermal conductivity compared to the metal needle has a thermal conductivity less than 1 W/m·K. Yet a further example is where the material having the substantially lower thermal conductivity compared to the metal needle has a thermal conductivity less than 0.5 W/m·K.

PEEK needles may have a thermal conductivity of about 0.25 W/m·K compared to a titanium needle that may have a thermal conductivity of about 21.9 W/m·K. During surgery, e.g. ophthalmic cataract surgery, a phaco needle is in physical contact with the patient's eye and cornea. The significant heat generated by the handpiece via vibrations of the transducers and horn may be thermally transferred to the patient's eye and cornea via the needle. Thermal damage, known as corneal burns, is known to occur occasionally. Thermal imaging of the needles during use in lab testing, showed increasing thermal levels progressing from the hub of the needle towards the tip; this supports the theory that the source of the heat causing corneal burns is within the handpiece and that the heat is conducted to the cornea along the needle shaft. Use of a material that is a poor thermal conductor, i.e. a material that has a substantially lower thermal conductivity compared to the metal needle may reduce or eliminate corneal burns and other deleterious effects of thermal build-up in the eye.

Another example phaco needle may include a hub for connection to an ultrasonic handpiece and an elongated shaft formed with the hub and extending from the hub wherein a distal end of the shaft breaks-up tissue when the distal end is caused to be vibrated by the handpiece, as described above. This example includes a needle where at least a distal portion of the shaft may be formed of a material having a substantially lower mechanical lateral stiffness compared to a metal needle.

Example phaco needles formed of material having a substantially lower mechanical lateral stiffness may have the same properties described above with respect to needle 10. That is the example needles may be transparent, may have integrally formed irrigation sleeves, may be formed of PEEK or other plastic materials, etc. Further, the material having the substantially lower mechanical lateral stiffness compared to the metal needle may have a mechanical lateral stiffness less than 10 GPa (Giga Pascals). Still further, the material having the substantially lower mechanical lateral stiffness compared to the metal needle may have a mechanical lateral stiffness less than 5 GPa. Even further, the material having the substantially lower mechanical lateral stiffness compared to the metal needle may have a mechanical lateral stiffness less than 2 GPa.

PEEK needles may have a shear modulus of about 1.3 GPa, substantially less than the prior art titanium phaco needles having a shear modulus of about 44 GPa. Lab experiments with PEEK phaco needles suggest that it is noticeably more difficult to break a capsular bag compared to a conventional titanium phaco needle. Thus, needles formed of a material having the substantially lower mechanical lateral stiffness compared to the metal needle may reduce the occurrence of unwanted capsular bag ruptures or other collateral tissue damage compared to the use of metal needles. The term mechanical lateral stiffness refers to a needle that displaces laterally at least some minimum specified distance (generally expressed in micrometers) in response to a lateral or shear stress (generally expressed in gigapascals). A material that has a lower mechanical lateral stiffness compared to another material may be said to be more compliant, i.e. the material gives or moves more easily when a force is applied to the material.

Shear modulus is the ratio of the shear stress (force per unit area) in a material and the lateral displacement, strain, (dimensionless, e.g. meters of displacement per meter of material). Lower shear modulus materials will deform more, i.e. transfer less force, when brought into contact with a surface compared to higher shear modulus materials. Hence, a needle made from a low shear modulus material will bend more as it comes in contact with the capsular bag compared to a conventional titanium needle.

Another example phaco needle may include a hub for connection to an ultrasonic handpiece and an elongated shaft formed with the hub and extending from the hub wherein a distal end of the shaft breaks-up tissue when the distal end is caused to be vibrated by the handpiece, as described above. This example includes a needle where at least a distal portion of the shaft may be formed of a material having a substantially higher efficiency of converting electrical energy powering the handpiece into motion of the distal end compared to a metal needle.

Example phaco needles formed of material having a substantially higher efficiency of converting electrical energy powering the handpiece into motion of the distal end compared to a metal needle may have the same properties described above with respect to needle 10. That is the example needles may be transparent, may have integrally formed irrigation sleeves, may be formed of PEEK or other plastic materials, etc. Further, the material having the substantially higher efficiency of converting electrical energy powering the handpiece into motion of the distal end compared to a metal needle may enable a peak to peak stroke of at least 120 μm (micrometers) with less than 5 W of electrical energy powering the handpiece when the needle is in an eye.

Typical known phaco handpiece systems employ a handpiece that is separable from a titanium needle and require 30 W or more of direct drive power (voltage current cosine of the phase angle between the voltage and current) to achieve strokes on the order of 120 μm peak to peak in simulated eye conditions (with the needle tip immersed to a depth less than the shaft length in water).

Phaco handpieces are typically driven with a linear amplifier, with theoretical power conversion efficiencies between 25% (for a single sided class A amplifier) and about 71% (for a class B amplifier optimized for maximum output at a specific load). In practice, accounting for potential variations in handpiece loads, results in suboptimal amplifier design. Providing 35 W of output drive power may require amplifier power supplies with output capacities between 70-100 watts. This high power supply requirement is a major factor preventing practical phaco handpieces from being driven by battery-powered drives and preventing cost-effective single use handpiece/needle designs. Such high gain systems (using materials that more efficiently convert electrical power into motion) may enable smaller handpieces, cooler operating temperatures for the handpieces, disposable handpieces, use of lower cost, greener plastic piezo transducer elements, and elimination of a need for a separable needle/horn.

Furthermore, because the mechanical-acoustic output of a handpiece with a tubular needle with an OD (outer diameter) of one mm or less and a stroke of 120-130 μm is well under 0.5 W, most of the approximately 30 W of electrical energy delivered to a typical conventional handpiece must be dissipated somewhere other than the active area of the tip. The energy dissipation may result from multiple factors, e.g. heating build-up in the handpiece, heating irrigation fluid flowing through the handpiece, or energy dissipated by the handpiece at or away from the surgical site after active drive to the handpiece has been turned off. In short, dissipation of the power created may result in clinically undesirable effects, e.g. thermal effects or limits on maximum pulsed activation rates. Therefore, the efficiency with which the handpiece coverts electrical power delivered to it into mechanical displacement (motion) of the tip may be a key design consideration.

Four important factors in designing a highly efficient ultrasonic handpiece include: choosing the correct geometry ultrasonic parts, minimizing the mechanical lateral stiffness of the material to be vibrated, minimizing the mass of the ultrasonic parts that will move the most (e.g. the needle, especially the needle distal tip, but also the other parts), and ensuring sufficient durability of the needle and/or handpiece to operate without mechanical failure for the expected duration of use.

Choosing the correct geometry essentially involves ensuring that the needle shaft (or distal end of the horn, if no separable needle is used) length is close to a quarter of the wavelength of the selected vibrating frequency in the selected material and is related to the speed of sound (c) for the particular material. This may be achieved by selecting two of the three parameters of length, frequency, and material and optimizing the third parameter. Minimizing the mechanical lateral stiffness of the material may be achieved by selecting materials with a low Young's modulus (E). Minimizing the mass of needle, especially the needle shaft, may be achieved by minimizing the density of the material ($\rho$) chosen. Ensuring sufficient durability of the needle is to say that the needle material must be strong enough. Sufficient durability may be achieved by calculating the anticipated stresses on the needle/horn plus a safety factor reflecting the expected duration of use and reviewing published values for the ultimate strength of possible materials to be used. In general, durability is important for product reliability, but may be viewed as more of a material selection review activity than a driver of the material selection. For example, in designing a needle/horn a material may be considered that enhances the first three factors, and only then would the ultimate strength of the material be checked or tested. As those skilled in the art will appreciate, picking a material for both a minimum E and a minimum $\rho$ results in some fixed value of c, which may not be correct for the chosen vibrating frequency and shaft length. All three values of E, $\rho$, and c are specific to each material and therefore, E and $\rho$ cannot be minimized independently; thus, some judgment must be employed when choosing a material.

In an example experiment, a needle was made from a plastic material, PEEK, instead of the conventional prior art titanium. The density of PEEK (1320 kg/m$^3$) is less than ⅓ of the density of titanium (4508 kg/m$^3$), and the Young modulus of PEEK (3.6 GPa) is less than ¹/₃₀ the Young modulus for titanium (116 GPa). The quarter wavelength of the PEEK (about 0.57 inches (in.) at 28.5 kHz assuming a speed of sound, c, of 1650 m/sec) was much more closely matched to the conventional titanium needle length of 0.755 in. and the needle shaft length of 0.57 in. than the quarter wave of the predicate titanium (requiring a needle length of about 1.75 in.). PEEK needles attached to a conventional ultrasonic phaco handpiece exhibited strokes in excess of 120 μm at drive powers between 2-3 W.

In another example the separable needle may be eliminated and designed into the horn, and the transducer may be made from a plastic material, appropriately matched to an integral horn/needle. Eliminating the screw-on needle eliminates the need to make the transducer wall thick enough to create mating internal threads; thereby reducing the mass of the primary mechanical gain component. By combining the function of the needle (insertion into the eye, with the distal end moving to emulsified tissue) with the transducer horn may result in a distal end with a smaller diameter and a thinner wall compared to prior art metal needles. Because the maximum stress required to create the necessary stroke of a combined needle/horn would be reduced significantly, the bolt portion of the ultrasonic components may be plastic (instead of the prior art metal, e.g. steel), and it is possible that the prior art piezo crystals could be changed to a thinner piezo-plastic, reducing cost and better matching the needle/horn materials structure.

Another example phaco needle may include a hub for connection to an ultrasonic handpiece and an elongated shaft formed with the hub and extending from the hub wherein a distal end of the shaft breaks-up tissue when the distal end is caused to be vibrated by the handpiece, as described above. This example includes a needle where at least a distal portion of the shaft may be formed of a material having a substantially lower acoustical impedance compared to a metal needle.

Example phaco needles formed of material having a substantially lower acoustical impedance compared to a metal needle may have the same properties described above with respect to needle 10. That is the example needles may be transparent, may have integrally formed irrigation sleeves, may be formed of PEEK or other plastic materials, etc. Further, the material having the substantially lower acoustical impedance compared to a metal needle may have an acoustical impedance of less than 20 MRayls (megarayls). Rayl is the common unit for acoustic impedance and is equal to a kg/m$^2$s. Still further, the material having the substantially lower acoustical impedance compared to the metal needle may have an acoustical impedance less than 10 MRayls. Even further, the material having the substantially lower acoustical impedance compared to the metal needle may have an acoustical impedance of less than 3 MRayls. Yet again, the material having the substantially lower acoustical impedance compared to the metal needle may have an acoustical impedance less than 1 MRayls. In another example, the material having the substantially lower acoustical impedance compared to the metal needle may have an acoustical impedance similar to an acoustical impedance of water.

The prior art material for the needle, titanium, has an acoustic impedance of around 22.8 MRayls, and therefore values less than 20 MRayls may be regarded as substantially lower. Comparatively, PEEK needle has an acoustic impedance of around 2.2 MRayls. It is noted that a phaco needle made from a material with relatively low values for other material properties may contribute to low acoustic impedance (Young's modulus and density) and achieve desirable operating characteristics as discussed above.

During surgery, e.g. ophthalmic cataract surgery, the distal end of the needle inserted into the eye transmits energy into the tissue and fluid around the tip. Inefficient transfer of energy to the tip results in the need for higher drive powers and heat generation, as previously discussed. Furthermore, when contemplating the generation of various lateral vibration modes in the needle via cross-coupling, high material acoustic impedances such as in titanium impede the effective coupling of energy from one vibration mode to another. The use of lower acoustical impedance materials increases the coupling of energy transfer.

Another example phaco needle may include a hub for connection to an ultrasonic handpiece and an elongated shaft formed with the hub and extending from the hub wherein a distal end of the shaft breaks-up tissue when the distal end is caused to be vibrated by the handpiece, as described above. This example includes a needle where at least a distal portion of the shaft may be formed of a material having a substantially higher Poisson's ratio compared to a metal needle.

Example phaco needles formed of material having a substantially higher Poisson's ratio compared to a metal needle may have the same properties described above with respect to needle 10. That is the example needles may be transparent, may have integrally formed irrigation sleeves, may be formed of PEEK or other plastic materials, etc. Further, the material having the substantially higher Poisson's ratio compared to a metal needle may have a Poisson's ratio, $\upsilon$, greater than 0.36. Still further, the material having the substantially higher Poisson's ratio compared to a metal needle may have a Poisson's ratio, $\upsilon$, greater than 0.4. Materials, with a relatively high Poisson ratio, produce additional motions in a direction perpendicular to the dominant direction of wave propagation in a phaco emulsification needle. For example, with a longitudinal transducer, a needle made or partially made from a material with high Poisson ratio will produce a radial vibration in addition to the longitudinal motion.

When a structure, e.g. a phaco needle, experiences mechanical vibration in one direction (e.g., longitudinal extension and contraction), because of the conservation of mass, there is a lateral vibration "induced" (e.g., a contraction and expansion). The lateral vibration may be characterized as elastic behavior and is largely determined by the material's Poisson ratio. Poisson's ratio is defined as the ratio of lateral to longitudinal strains, where strain represents a change in length versus an initial length.

The Poisson ratio for most metals known to be used for surgical ultrasonic needles is around 0.3 (e.g. titanium is approximately 0.345); however, other types of materials (softer or structured) may have Poisson ratios up to 0.5 (or even negative values). Forming a phaco needle or a portion of the needle from a material with Poisson ratio larger than that of titanium will result in a more pronounced radial vibration. A Poisson ratio for plastics, e.g. PEEK is about 0.45, or about 50% higher than metals.

For instance, in a longitudinal ultrasound transducer, as a standing waves produces longitudinal strokes, the Poisson Effect induces a "chewing" or "pumping" effect, with the same frequency as the drive frequency and an amplitude proportional to the drive wave that is 180 degrees out of phase difference, i.e. the needle's longitudinal-extension corresponds to its radial-contraction. If in addition to designing a needle material for a high Poisson ratio, a needle is designed to produce a high gain, the needle's radial motion may be enhanced.

The relative volume displaced by a radial motion in the inner-diameter (ID) the needle shaft may be substantial, because the cross-sectional area normal to the direction of motion is large and because the fluid is working (symmetrically) against the diametrically opposed wall through a largely incompressible fluid. Therefore, a needle formed or partially formed of a relatively high Poisson ratio material may be significantly more efficient transferring energy to the fluid compared to a metal needle. More efficient energy transfer potentially allows for lower drive powers to be used to emulsify tissue.

The radial motion effect will be largest at the longitudinal vibration nodal points, where longitudinal strain is highest; ensuring that these longitudinal nodes fall along the needle shaft should enhances the effect considerably. For a first order, the radial strain $S_r$ will be equal to $\upsilon_m \cdot S_1$, where $\upsilon_m$ is the Poisson ratio of the material and $S_1$ is the longitudinal strain.

Those skilled in the art will appreciate that some other material properties may work in concert with this Poisson's ratio property to further enhance the radial motion effect. For instance, a material with low acoustic impedance and an area under strain near a lateral wave node may help create a radially symmetric resonant standing shear wave with even greater amplitude at the distal end of the needle; even though the longitudinal strain at the needle distal end is low. This combination of material properties and needle shaft length design may result in relatively little radially symmetric displacement being induced directly by longitudinal strain at the lateral wave node.

Another example phaco needle may include a hub for connection to an ultrasonic handpiece and an elongated shaft formed with the hub and extending from the hub wherein a distal end of the shaft breaks-up tissue when the distal end is caused to be vibrated by the handpiece, as described above. This example includes a needle where the elongated shaft 14 has a free shaft length 40 (see FIG. 1) and is formed with the hub 20 and extends from the hub. A distal end 16 of the shaft breaks-up tissue when the distal end is caused to be vibrated by the handpiece at a given range of frequencies. At least a distal portion 18 of the shaft 14 may be formed of a material having a substantially higher mechanical gain compared to a metal needle vibrated by the handpiece and having a metal free shaft length substantially the same as the elongated free shaft length.

Example phaco needles formed of material having a substantially higher mechanical gain compared to a metal needle may have the same properties described above with respect to needle 10. That is the example needles may be transparent, may have integrally formed irrigation sleeves, may be formed of PEEK or other plastic materials, etc. The term gain, in this example, refers to an increase in displacement distance from the displacement distance at an input interface to the displacement difference at an output interface. Further, the material having a substantially higher mechanical gain compared to a metal needle may have a gain greater than 2. Still further, the material having a substantially higher mechanical gain compared to a metal needle may have a gain greater than 10. For example, with a straight phaco needle, vibrated longitudinally, formed from material with a lower mass and higher compliance compared to metal phaco needles, and with a free shaft length approximately equal to the quarter wavelength of the operating frequency will have a significant amount of gain in the needle's free shaft length. If the needle free shaft length (measured from an end of any taper of the shaft to the hub) is between about 23.4% and 26.7% of the wavelength of a frequency in the needle material the needle gain will be greater than 10. That is the needle distal end has a stroke distance of approximately 120 µm from a transducer stroke of 12 µm when vibrated by the handpiece and a power required to drive the handpiece is substantially less than a power required to drive the handpiece with the metal needle with a substantially similar stroke distance. Such a needle requires a small fraction of the drive power required to produce similar strokes using metal needles. For example, where the elongated free shaft length is approximately 0.57 inches, the power required to drive the handpiece is less than 10 watts. In fact, where the elongated free shaft length is approximately 0.57 inches, the power required to drive the handpiece is less than 5 watts.

Three examples of designing a needle follow. A first example includes choosing a vibration frequency and a needle material, and then using the disclosed construction parameters to identify an optimal needle length. A second example is especially useful for designing needles to be used with existing handpiece and sleeve combinations. In the second example, the desired needle length may have already been determined, along with the vibrating frequency; leaving the designer with selecting a needle material that ensures the final configuration approximates the disclosed optimal construction parameters. A third example includes selecting a needle material (metal or non-metal) and the needle length (based on existing handpiece and sleeve geometries) and then determining the drive frequency to approximate optimal performance.

An example using the second design example may be a needle for a 28.5 kHz drive frequency, where the needle length is 0.755 inches from the transducer flange to the distal end and the needle free shaft length is approximately 0.57 inches. Prior art needles of this type have been manufactured from metal, typically titanium. However, a titanium needle with a 28.5 kHz drive frequency has a quarter wavelength of about 1.75 inches, resulting in a fairly low gain of about 1.2.-1.3. If PEEK material is selected, a quarter wave wavelength at 28.5 kHz is approximately 0.57 inches (very close to the standard prior art free shaft length). The wavenumber of the PEEK needle is about 1.57 radians, and the resulting theoretical needle gain is in excess of 1000. In testing, drive powers for a prior art handpiece creating PEEK needle strokes in excess of 120 µm in air were less than 3 W, in stark contrast to 20 W drive levels required for the same handpiece to produce similar stroke distances with a titanium needle.

An example using the third method may include selecting an optimal drive frequency for the 0.755 inch titanium needle. Optimizing based on the free shaft length of 0.57 inches, results in a drive frequency of about 88 kHz; while optimizing based on the total needle length of 0.755 inches results in a drive frequency of about 65 kHz. Lab experiments showed that such a titanium needle may be driven in a highly efficient manner (high stroke at low power) at about 76 kHz, which is between the range of drive frequencies determined for the free shaft length and the total needle length.

It is believed that bevels at the free end of the needle, bends in the shaft, and the radius at the taper at the shaft interface with the hub all influence the standing wave slightly. These additional influences result in some deviations from the quarter wavelength identified in the examples above. Adjusting either the drive frequency or the final needle dimensions slightly to achieve the best performing needle may be needed.

Needle gain for a simple tube model of the needle (uniform cross sectional area along the entire length) may be calculated from the equation:

$$G = 1/\sin((\pi/2) - k)$$

where $k = 2\pi * \text{length}/\lambda(\text{material+frequency}) = 2\pi * \text{length} * \text{frequency}/c(\text{material})$; $\lambda(\text{material+frequency})$ is the wavelength of sound at the drive frequency in the material; and c(material) is a speed of sound in the material and generally may be considered as:

$$c(\text{material}) = (E/\rho)0.5$$

where E is Young's modulus of the material and ρ is the density of the material

It is believe that the most influential longitudinal dimension to be used for needle length may be the free shaft length from the intersection of any taper radius and the shaft, where the cross-sectional area is minimized, or alternatively (in cases where the needle cross sectional area varies), the distance from the distal end of the needle to the most proximal minimum cross sectional area along the needle. For more complex shapes, such as needles with tapered hubs and where the cross sectional area changes along the needle length but the material stays homogeneous, gain may be calculated using a finite element model. In general, optimal needle gain is achieved by keeping the shaft area relatively small on the distal side of the node formed along the needle at a particular frequency compared to the shaft area on the proximal side of the node. Such a design creates a needle that is relatively stiff and non-compliant on the proximal side of the node, meaning that the needle portion proximal to the node minimizes absorption of the motion of the driver.

The term transparent, as used in the disclosed examples, refers to a needle or a portion of a needle that is formed from an optically clear material. For example, tests of needles formed from Ultem™ (polyetherimide) were found to have a light transmission of 58% per the ASTM D 1003 standard test method. Transparent needles, unlike the opaque prior art needles, provide a surgeon visibility of fluids and tissue being aspirated through the needle, including bubbles, and clogging issues. Materials that have a light transmission of more than 15%, i.e. a transmission percentage at which an air bubble inside the needle is formed may be considered to be transparent. Transparent needles may also allow ruler patterns to be molded along the needle length, allowing a surgeon to quickly estimate a capsularhexis diameter or a depth of the capsular bag. Transparent needles may be clear or tinted a variety of colors. Of course, if an irrigation sleeve is formed or used with the transparent needle, the irrigate sleeve may also be formed of a transparent material.

As mentioned throughout the example disclosures, an ultrasonic needle may be formed from multiple materials. High material strength and biocompatibility are a couple of reasons why historically titanium (and titanium alloys) has been the dominant material used to fabricate ultrasonic phaco needles. A phaco needle is the medium through which the vibration from a piezo-stack and horn is transferred to a cataract and other tissue to be emulsified and aspirated. Ultrasonic energy transfer, including directivity and efficiency, depends on both the material properties and structural design of a needle. For example, a straight needle design made from titanium alloy (e.g. Ti6A14V, Young modulus: ~116 GPa) transmits longitudinal, lateral, or torsional movements (the major direction of movement depends on the handpiece design) from the piezo-stack (or transducer) to the surgical site with negligible loss or deviation in the primary direction of the movement. Many other needle structures are well-known and may include but are not limited to bent, curved, flared, off-set shafts, non-symmetrical weight distribution, various cross-sectional shapes, etc., with virtually all the various phaco needle designs being formed from metal, especially titanium.

Utilizing other materials may benefit surgery by allowing emulsification of cataracts and other tissue at lower ultrasound power settings compared to the known titanium needles. For example, a two-segment needle may be formed where the first segment may be made from a stiff material (e.g. Young modulus >~5 GPa) such as Torlon® and a second segment made from a less stiff material (e.g. Young modulus <~3 GPa) such as PMMA (polymethyl methacrylate). The first segment, made from a stiff material, may be the proximal portion of needle that extends distally so that the stiff material will generally be in contact with the incision site and the second segment of less stiff material may be the distal portion (e.g. 18 of FIG. 1) that is inserted into the eye and contacts the cataract and other tissue to be removed.

The higher elasticity (i.e. lower Young modulus) of the second segment, as discussed above, results in (a) secondary lateral movements (in addition to the primary longitudinal needle movement) at the tip of the needle for improved emulsification of tissue and (b) an improved safety profile because, based on lab experiments, the less stiff material reduces the risk of rupture in the posterior capsule when the needle impacts the capsule bag compared to a comparably shaped titanium needle. Forming a needle of multiple materials may allow the selection of the first segment material so that friction between the cornea at the incision site and the needle is minimized. Furthermore, selecting the material for the second segment at the needle distal end may allow for a material where the portion of vibration energy transferred into strain energy (i.e., thermal energy) is enhanced. Intentionally generating localized thermal energy at the needle distal end but minimizing any thermal energy in the first segment may improve liquefaction (reducing viscosity and surface tension) of the fibrous structure of cataract while minimizing the risk of thermal damage to the cornea. A multi-segment phaco needle may be manufactured using any known methods, e.g. a 2-shot micro-molding process.

The multiple material example above was with respect to movement of a straight needle with a primary ultrasonic vibration generated by the transducer, in a longitudinal direction. The multi-material phaco needle benefits may also apply to other transducer designs having primary vibration movements in angular (torsional), lateral, or a combination of directions.

A phaco transducer assembly, such as shown in FIG. 2, may include a reflector and a driver connected to the reflector for vibrating at a range of frequencies and at a known power level. A horn may be connected to the driver opposite the reflector. A needle may be connected to the horn opposite the driver and the needle further has a distal end. The needle may have a free shaft length substantially equal to a quarter-wavelength of the speed of sound through materials forming the needle at the driver vibrating range of frequencies. A construction of the transducer assembly to achieve a desired stroke length at the needle distal end depends on at least three factors, including the driver vibrating range of frequencies, the free shaft length of the needle, and the materials forming the needle; such that for any two of the three factors known, the remaining third factor may be determined.

Consider an example where the desired stroke length is approximately 120 μm, the range of frequencies at which the driver will vibrate are at a nominal frequency of about 28.5 kHz, and the free shaft length of the needle is approximately 0.57 inches. The material forming the needle may then be determined as a material having the quarter-wavelength of the speed of sound through that material of approximately 0.57 inches at the nominal frequency of about 28.5 kHz. An example of such material is PEEK.

Another example phaco transducer assembly, such as shown in FIG. 2, may include a reflector and a driver connected to the reflector, the driver having a known driver vibration frequency range. A horn may be connected to the driver opposite the reflector. A needle may be connected to the horn opposite the driver, where the needle has a known free shaft length. To maximize a desired stroke length of the needle for a minimal amount of power applied to the driver, a material forming the needle may be chosen such that a speed of sound through the material results in a quarter-wavelength distance at the driver vibration frequency range substantially equal to the needle free shaft length.

Some additional example embodiments according to the above disclosure are set forth below.

An first example phacoemulsification needle may include: a hub for connection to an ultrasonic handpiece; an elongated shaft formed with the hub and extending from the hub wherein a distal end of the shaft breaks-up tissue when the distal end is caused to be vibrated by the handpiece; and wherein at least a distal portion of the shaft is formed of a material having a substantially higher electrical resistivity compared to a metal needle.

The first example, wherein at least the distal portion is substantially transparent.

The first example, wherein an irrigation sleeve is integrally molded with at least the distal portion.

The first example, wherein the needle is entirely formed of the material having the substantially higher electrical resistivity compared to the metal needle.

The first example of the previous paragraph, wherein a horn of the handpiece is also formed of the material having the substantially higher electrical resistivity compared to the metal needle.

The first example, wherein at least the distal portion is formed of a plastic material.

The first example, wherein the plastic material is polyether ether ketone.

The first example, wherein the material having the substantially higher electrical resistivity compared to the metal needle has an electrical resistivity greater than 1 µΩ·m.

The first example, wherein the material having the substantially higher electrical resistivity compared to the metal needle has an electrical resistivity greater than 500,000 µΩ·m.

A second example phacoemulsification needle may include: a hub for connection to an ultrasonic handpiece; an elongated shaft formed with the hub and extending from the hub wherein a distal end of the shaft breaks-up tissue when the distal end is caused to be vibrated by the handpiece; and wherein at least a distal portion of the shaft is formed of a material having a substantially lower thermal conductivity compared to a metal needle.

The second example, wherein at least the distal portion is substantially transparent.

The second example, wherein an irrigation sleeve is integrally molded with at least the distal portion.

The second example of the previous paragraph, wherein the needle is entirely formed of the material having the substantially lower thermal conductivity compared to the metal needle.

The second example, wherein a horn of the handpiece is also formed of the material having the substantially lower thermal conductivity compared to the metal needle.

The second example, wherein at least the distal portion is formed of a plastic material.

The second example, wherein the plastic material is polyether ether ketone.

The second example, wherein the material having the substantially lower thermal conductivity compared to the metal needle has a thermal conductivity less than 18 W/m·K.

The second example, wherein the material having the substantially lower thermal conductivity compared to the metal needle has a thermal conductivity less than 10 W/m·K.

The second example, wherein the material having the substantially lower thermal conductivity compared to the metal needle has a thermal conductivity less than 5 W/m·K.

The second example, wherein the material having the substantially lower thermal conductivity compared to the metal needle has a thermal conductivity less than 1 W/m·K.

The second example, wherein the material having the substantially lower thermal conductivity compared to the metal needle has a thermal conductivity less than 0.5 W/m·K.

A third example phacoemulsification needle may include: a hub for connection to an ultrasonic handpiece; an elongated shaft formed with the hub and extending from the hub wherein a distal end of the shaft breaks-up tissue when the distal end is caused to be vibrated by the handpiece; and wherein at least a distal portion of the shaft is formed of a material having a substantially lower mechanical lateral stiffness compared to a metal needle.

The third example, wherein at least the distal portion is substantially transparent.

The third example, wherein an irrigation sleeve is integrally molded with at least the distal portion.

The third example, wherein the needle is entirely formed of the material having the substantially lower mechanical lateral stiffness compared to the metal needle.

The third example, wherein a horn of the handpiece is also formed of the material having the substantially lower mechanical lateral stiffness compared to the metal needle.

The third example, wherein at least the distal portion is formed of a plastic material.

The third example, wherein the plastic material is polyether ether ketone.

The third example, wherein the material having the substantially lower mechanical lateral stiffness compared to the metal needle has a mechanical lateral stiffness less than 10 GPa.

The third example, wherein the material having the substantially lower mechanical lateral stiffness compared to the metal needle has a mechanical lateral stiffness less than 5 GPa.

The third example, wherein the material having the substantially lower mechanical lateral stiffness compared to the metal needle has a mechanical lateral stiffness less than 2 GPa.

A fourth example phacoemulsification needle may include: a hub for connection to an ultrasonic handpiece; an elongated shaft formed with the hub and extending from the hub wherein a distal end of the shaft breaks-up tissue when the distal end is caused to be vibrated by the handpiece; and wherein at least a distal portion of the shaft is formed of a material having a substantially higher efficiency of converting electrical energy powering the handpiece into motion of the distal end compared to a metal needle.

The fourth example, wherein at least the distal portion is substantially transparent.

The fourth example, wherein an irrigation sleeve is integrally molded with at least the distal portion.

The fourth example, wherein the needle is entirely formed of the material having the substantially higher efficiency of converting electrical energy powering the handpiece into motion of the distal end compared to the metal needle.

The fourth example, wherein a horn of the handpiece is also formed of the material having the substantially higher efficiency of converting electrical energy powering the handpiece into motion of the distal end compared to the metal needle.

The fourth example, wherein at least the distal portion is formed of a plastic material.

The fourth example, wherein the plastic material is polyether ether ketone.

The fourth example, wherein the material having the substantially higher efficiency of converting electrical energy powering the handpiece into motion of the distal end compared to the metal needle enables a peak to peak stroke of at least 120 µm with less than 5 W of electrical energy powering the handpiece when the needle is in an eye.

A fifth example phacoemulsification needle may include: a hub for connection to an ultrasonic handpiece; an elongated shaft formed with the hub and extending from the hub wherein a distal end of the shaft breaks-up tissue when the distal end is caused to be vibrated by the handpiece; and wherein at least a distal portion of the shaft is formed of a material having a substantially lower acoustical impedance compared to a metal needle.

The fifth example, wherein at least the distal portion is substantially transparent.

The fifth example, wherein an irrigation sleeve is integrally molded with at least the distal portion.

The fifth example, wherein the needle is entirely formed of the material having the substantially lower acoustical impedance compared to the metal needle.

The fifth example, wherein a horn of the handpiece is also formed of the material having the substantially lower acoustical impedance compared to the metal needle.

The fifth example, wherein at least the distal portion is formed of a plastic material.

The fifth example, wherein the plastic material is polyether ether ketone.

The fifth example, wherein the material having the substantially lower acoustical impedance compared to the metal needle has an acoustical impedance of less than 20 MRayls.

The fifth example, wherein the material having the substantially lower acoustical impedance compared to the metal needle has an acoustical impedance less than 10 MRayls.

The fifth example, wherein the material having the substantially lower acoustical impedance compared to the metal needle has an acoustical impedance of less than 3 MRayls.

The fifth example, wherein the material having the substantially lower acoustical impedance compared to the metal needle has an acoustical impedance less than 1 MRayls.

The fifth example, wherein the material having the substantially lower acoustical impedance compared to the metal needle has an acoustical impedance similar to an acoustical impedance of water.

A sixth example phacoemulsification needle may include: a hub for connection to an ultrasonic handpiece; an elongated shaft formed with the hub and extending from the hub wherein a distal end of the shaft breaks-up tissue when the distal end is caused to be vibrated by the handpiece; and wherein at least a distal portion of the shaft is formed of a material having a substantially higher Poisson's ratio compared to a metal needle.

The sixth example, wherein at least the distal portion is substantially transparent.

The sixth example, wherein an irrigation sleeve is integrally molded with at least the distal portion.

The sixth example, wherein the needle is entirely formed of the material having the substantially higher Poisson's ratio compared to the metal needle.

The sixth example, wherein a horn of the handpiece is also formed of the material having the substantially higher Poisson's ratio compared to the metal needle.

The sixth example, wherein at least the distal portion is formed of a plastic material.

The sixth example, wherein the plastic material is polyether ether ketone.

The sixth example, wherein the material having the substantially higher Poisson's ratio compared to the metal needle has a Poisson's ratio greater than 0.36.

The sixth example, wherein the material having the substantially higher Poisson's ratio compared to the metal needle has a Poisson's ratio greater than 0.4.

A seventh example phacoemulsification needle may include: a hub for connection to an ultrasonic handpiece; an elongated shaft having a free shaft length and formed with the hub and extending from the hub wherein a distal end of the shaft breaks-up tissue when the distal end is caused to be vibrated by the handpiece at a given range of frequencies; and wherein at least a distal portion of the shaft is formed of a material having a substantially higher mechanical gain compared to a metal needle vibrated by the handpiece and having a metal free shaft length substantially the same as the elongated free shaft length.

The seventh example, wherein at least the distal portion is substantially transparent.

The seventh example, wherein an irrigation sleeve is integrally molded with at least the distal portion.

The seventh example, wherein the needle is entirely formed of the material having the substantially higher mechanical gain compared to the metal needle.

The seventh example, wherein a horn of the handpiece is also formed of the material having the substantially higher Poisson's ratio compared to the metal needle.

The seventh example, wherein at least the distal portion is formed of a plastic material.

The seventh example, wherein the plastic material is polyether ether ketone.

The seventh example, wherein the material having the substantially higher mechanical gain compared to the metal needle has a mechanical gain greater than 2.

The seventh example, wherein the material having the substantially higher mechanical gain compared to the metal needle has a mechanical gain greater than 10.

The seventh example, wherein the needle distal end has a stroke distance of approximately 120 µm when vibrated by the handpiece and a power required to drive the handpiece is substantially less than a power required to drive the handpiece with the metal needle with a substantially similar stroke distance.

The seventh example, wherein the elongated free shaft length is approximately 0.57 inches and the power required to drive the handpiece is less than 10 watts.

The seventh example, wherein the elongated free shaft length is approximately 0.57 inches and the power required to drive the handpiece is less than 5 watts.

A first example phacoemulsification transducer assembly may include: a reflector; a driver connected to the reflector for vibrating at a range of frequencies and at a known power level; a horn connected to the driver opposite the reflector; a needle connected to the horn opposite the driver and having a distal end and having a free shaft length substantially equal to a quarter-wavelength of the speed of sound through materials forming the needle at the driver vibrating range of frequencies; and wherein a construction of the transducer assembly to achieve a desired stroke length at the distal end depends on at least three factors including the driver vibrating range of frequencies, the free shaft length of the needle, and the materials forming the needle, such that for any two of the three factors known, the remaining third factor may be determined.

The first example transducer assembly, wherein the desired stroke length is approximately 120 µm, the range of frequencies at which the driver will vibrate are at a nominal frequency of about 28.5 kHz, and the free shaft length of the needle is approximately 0.57 inches and therefore the material forming the needle is determined as a material having the quarter-wavelength of the speed of sound through that material of approximately 0.57 inches at the nominal frequency of about 28.5 kHz.

A second example phacoemulsification transducer assembly may include: a reflector; a driver connected to the reflector, the driver having a known driver vibration frequency range; a horn connected to the driver opposite the reflector; a needle connected to the horn opposite the driver, the needle having a known free shaft length; and wherein to maximize a desired stroke length of the needle for a minimal amount of power applied to the driver, a material forming the needle is chosen such that a speed of sound through the material results in a quarter-wavelength distance at the driver vibration frequency range substantially equal to the needle free shaft length.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A phacoemulsification transducer assembly comprising:
    a reflector;
    a driver connected to the reflector, the driver having a known driver vibration frequency range;
    a horn connected to the driver opposite the reflector;
    a needle connected to the horn opposite the driver, the needle having a known free shaft length; and
    wherein to maximize a desired stroke length of the needle for a minimal amount of power applied to the driver, a material forming the needle is chosen such that a speed of sound through the material results in a quarter-wavelength distance at the driver vibration frequency range substantially equal to the needle free shaft length.

2. A phacoemulsification transducer assembly comprising:
    a reflector;
    a driver connected to the reflector for vibrating at a range of frequencies and at a known power level;
    a horn connected to the driver opposite the reflector;

a needle connected to the horn opposite the driver and having a distal end and having a free shaft length substantially equal to a quarter-wavelength of the speed of sound through materials forming the needle at the driver vibrating range of frequencies; and wherein a construction of the transducer assembly to achieve a desired stroke length at the distal end depends on at least three factors including the driver vibrating range of frequencies, the free shaft length of the needle, and the materials forming the needle, such that for any two of the three factors known, the remaining third factor may be determined.

3. The phacoemulsification transducer assembly of claim 2 wherein the driver vibrating range of frequencies are at a nominal frequency of about 28.5 kHz and the free shaft length of the needle is approximately 14.5 mm and a material forming the needle is determined as a material having the quarter-wavelength of the speed of sound through that material of approximately 14.5 mm at the nominal frequency of about 28.5 kHz.

* * * * *